(12) United States Patent
Clark

(10) Patent No.: US 7,826,046 B1
(45) Date of Patent: Nov. 2, 2010

(54) METHOD AND APPARATUS FOR DETECTING CONTAMINATES ON A HARD SURFACE

(76) Inventor: Joseph T. Clark, 8 Armstrong Cir., Newtown, PA (US) 18940

( * ) Notice: Subject to any disclaimer, the term of this patent is extended or adjusted under 35 U.S.C. 154(b) by 0 days.

(21) Appl. No.: 12/433,973

(22) Filed: May 1, 2009

(51) Int. Cl.
*G01N 21/00* (2006.01)
(52) U.S. Cl. ................. 356/237.1; 356/237.3
(58) Field of Classification Search ..... 56/237.1–241.6, 56/335–344; 356/237.1–241.6, 335–344
See application file for complete search history.

(56) References Cited

U.S. PATENT DOCUMENTS

| | | | | |
|---|---|---|---|---|
| 1,621,645 A | * | 3/1927 | Thorp | ............ 362/396 |
| 2,599,253 A | * | 6/1952 | Gits | ............ 362/208 |
| 3,747,154 A | * | 7/1973 | O'Neil | ............ 15/264 |
| 4,586,741 A | * | 5/1986 | Muti | ............ 294/19.1 |
| 5,970,633 A | * | 10/1999 | Jones et al. | ............ 36/136 |

OTHER PUBLICATIONS

CARTERPRODUCTS.COM, "SP21 Six Lamp Inspection Lights by Carter Products", Carter Products Co., Inc., Grand Rapids, MI, 2 pages, 2007.
DOYLESYSTEMS.COM, "Doyle Systems—Visual Inspection Systems and Print Inspection Systems", Doyle Systems, 3 pages 2007.

* cited by examiner

*Primary Examiner*—Gregory J Toatley
*Assistant Examiner*—Jarreas C Underwood
(74) *Attorney, Agent, or Firm*—Florek & Endres PLLC

(57) ABSTRACT

A method and apparatus for detecting small particulate matter and contaminants on hard surfaces.

18 Claims, No Drawings

METHOD AND APPARATUS FOR DETECTING CONTAMINATES ON A HARD SURFACE

FIELD OF THE INVENTION

This invention relates to a method and apparatus for detecting contaminates on a surface. More specifically, the invention relates to a method for detecting small particulate matter and/or contaminants on a hard surface comprising directing a beam of light from a light source onto a hard surface. The beam of light is directed onto the hard surface at an acute angle. The beam of light will reflect off the hard surface and illuminate the small particulates or contaminates that are not readily visible when illuminated by conventional floor, wall, ceiling or table light source. The apparatus comprises a light source, such as a flashlight, attached to a moveable platform so the beam of light from the light source impinges upon the hard surface at an acute angle.

BACKGROUND OF THE INVENTION

Unhygienic floors and countertops are a dilemma in the house as well as at the workplace and can pose many health and safety risks. Almost all private households and public facilities such as restaurants, hospitals, cafeterias, prisons, schools, and manufacturing facilities require clean and hygienic work areas. Clean and hygienic work areas improve health and reduce safety risks.

A study reported in the December 2005 American Journal of Respiratory and Critical Care Medicine indicated that endotoxins associated with certain gram negative bacteria commonly found in household dust pose a significant risk for asthma. According to the authors, inhalation exposure to endotoxins is common in homes from sources such as dust (among other things). Peter S. Thorne, Ph.D., of the Environmental Health Sciences Research Center at the University of Iowa, Iowa City, and his associates evaluated 831 homes selected to represent the demographic characteristics of the U.S. population. The investigators took 2,552 house dust samples from five locations within the homes, including bedroom floors, bedding, family room floors, sofa surfaces, and kitchen floors. The authors found the strongest relationship between asthma, asthma medications, and wheezing came from endotoxin levels in bedroom floor and bedding dust. However, the effects were observed only in adults and not in children. Moreover, the investigators also noted that the endotoxin concentrations were highest in kitchen and living room floor dust. The investigators reported a mean concentration of endotoxin in kitchen floor dust that was 2.3-fold higher than the mean concentration of endotoxin in bedroom floor dust and 4.3-fold higher mean concentration of endotoxin in bedding dust. Clearly, effectively removing and eliminating dust and other small particulate and contaminants from hard surfaces can improve health conditions.

As far as safety risks are concerned, many slips can occur when floors are unclean. Slips are one of the most common causes of major injuries at work and the costs to industry are significant. Almost all slips happen when floors are dirty or wet, contaminated with water, oil, food, dust, lint, sand, plastic or any other debris effecting floor friction. In many nations, there are legal requirements that require floor surfaces to be suitable. Attention to preventing contamination from ever happening in the first place is clearly preferable and having the necessary tools that enable one to monitor contamination is just as important. Even very small amounts of contamination (one piece of small plastic or patch of dust) can have dramatic consequences depending upon the environment. Because of this, floor cleaning is a necessity.

Cleaning is very important in controlling many issues as evidenced by the 100+ billion dollar U.S. Commercial and Residential Cleaning Market. America purchases many products including vacuum cleaners, brooms, mops, dust pans, SWIFFERS® and cleansing chemicals. However, one shortcoming of current methods is that no matter how much cleaning gets done, the user is never truly assured that the surface is thoroughly contaminate free. Improving the current cleaning procedures and methods used by people and cleaning services is needed.

There's currently no effective method to help with quality control. Some vacuum cleaners have particle sensors that claim the ability to detect a clean surface. Also, many vacuums have a built in light that can illuminate a large area around the vacuum. These built in lights may aid in detecting floor contaminates however the illumination provide is often improperly directed and insufficiently focused to effectively detected and/or illuminate small contaminates on the floor. For example, the light source on vacuum cleaners typically focuses from above the floor being vacuumed thereby illuminating a wide area with a dispersed or diffused beam. In addition, when vacuuming hard surfaces, many vacuum manufacturers recommend and offer the ability to turn off the brush bar engine to avoid damaging bare floors and in doing so turns off the built in light as well.

Prior methods used for detecting contaminates on hard surfaces are not very effective. For example, the common "white glove" test only checked a small area. Often the contaminants are tiny, transparent or camouflaged (e.g. clear plastic, glass and hair) and are hard to detect on a "white glove" inspection. Natural light, ceiling lights, wall lights, table lamps, chandeliers, etc, also are not effective for locating small particulate matter on hard surfaces because the light is too diffused and/or not focused in a proper manner to illuminate small particulates and contaminants such as dirt and dust particles.

Therefore, there is a need for a method and apparatus that can be used to easily detect contaminates on hard surfaces and help avoid many health and safety risks caused by the contaminates. The present invention overcomes these drawbacks and fills these and other needs.

SUMMARY OF THE INVENTION

It is the general object of the present invention to provide a method and apparatus that quickly and efficiently detects small particulates and contaminates on hard surfaces such as floors and counter tops.

It is a further object of the present invention to provide a small particulate and contaminant detecting apparatus that is simple and easy to use that affords the user the ability to reduce cleaning time.

It is an additional object of the present invention to provide a method that is capable of detecting contaminates such as glass, water or oil that are typically camouflaged and not visible when relying on prior methods of exposure.

It is still a further object of the present invention to help promote and improve the wellbeing of private residences and public institutions by aiding in the removal of dust, dirt and hair particles from the environment.

It is another object of the present invention to provide a method for quickly spot-checking hard surfaces such as floors to ensure the surfaces are contaminate free.

It is still another object of the present invention to allow one to quickly superintend cleaning services in the public sector (i.e. cafeterias, schools, hospitals, etc.).

It is still a further object of the present invention to aid cleaning services with the ability to inspect their own efforts and support their guarantee of a clean surface.

It is another object of the present invention to educate people in both public and private sectors as to how quickly and how much dust and other contaminates can accumulate over time.

DETAILED DESCRIPTION OF THE INVENTION

These and other objects of the present invention are achieved by combining a portable light source, preferably a high powered durable light source, with a moveable platform so the beam of light emitted from the light source contacts the hard surface being cleaned at an acute angle. One embodiment of the present invention is useful on hard, smooth and level surfaces.

Embodiments of the light source can be a flashlight, an LED or other conventional known light sources such as an incandescent, fluorescent or high intensity discharge lamp. It is preferred that the light source provide a focused beam of light, most preferably in a single direction. Typically the light source is equipped with a reflective surface that reflects and concentrates the illumination into a single direction, i.e. less than 180°, preferably less 150° and most preferably less than 130° when viewed from above.

The following commercially available light sources were successfully tried on various embodiments of the present invention; SureFire G2® Nitrolon®, a high-intensity, incandescent flashlight with 65 lumen output; SureFire G2® LED, a high-intensity, 80 lumen output flashlight, equipped with a P60L reflector assembly lamp; INOVA T4™, a high-powered LED flashlight equipped with the TIROS™ Optical System with 100 lumen output. Based upon the testing conducted on these light sources, preferred embodiments of the present invention will employ a light source that exhibits at least 50 lumens or more and preferably 65 lumens or more.

The light source may further include a directional lens that allows a more focused and concentrated beam of light to be emitted from the light source. For example, the circular lens of a conventional flashlight may be covered with an opaque material wherein a rectangular opening has been formed in the opaque covering to further direct, concentrate and form the emitted light beam.

The light source may also feature a wired or unwired on/off remote controller. One embodiment of the remote controller preferably is a wireless controller with dimensions similar to conventional key fobs that control the locks on automobiles. The remote controller for the light source of the present invention should be designed to easily accommodate a users hand or user's clothing pocket. The remote controlled may also be designed to be removably attached to a user's pants, belt, or belt loop or a portion of the movable platform, such as the handle.

As used herein the term "acute angle" means the emitted light beam should create an angle of contact with the hard surface that is less than 35° when measured from the hard surface to the base of the light source. Preferably the acute angle should be less than 30° and most preferably less than 25°. In certain embodiments, the contact angle for the emitted light source should be about 0° to about 20°, preferably about 0° to about 15° and most preferably about 0° to about 10°.

The movable platform on which the light source is attached can be any type of solid structure that allows the emitted beam of light to contact the hard surface being cleaned at an acute angle and also to be easily moved. Some examples of moveable platforms that may be used in the present invention include but are not limited to feet, shoes, poles, sticks or vacuum cleaners. One embodiment of the present invention will attach the light source to a dust pan to insure all the small particulate and contaminate matter is removed from the hard surface. An alternative embodiment attaches the light source to a bucket, such as a rolling mopping bucket, employed in most commercial establishments. This embodiment allows the individual mopping a floor to quickly and easily verify that the area being mopped has been cleaned of all small particulate matter and contaminants prior to mopping. Another alternative embodiment of this invention will consist of varying means of attaching the light source to the side of a vacuum cleaner in a way that achieves directing the light beam at an acute angle onto the hard surface.

In an alternate embodiment of the present invention, the light source is attached, preferably in a removable manner, to a foldable or collapsible stick or pole that can be folded or collapsed to a small and storable size when not in use. A preferred embodiment will have the light source, such as a flashlight, rotatably attached to a telescoping, i.e., foldable or collapsible stick or pole, so the entire structure can be folded or collapsed into a small compact shape for storage and transport, but easily unfolded or expanded for use.

The apparatus of the invention should be easy to use and care for. The strength of the light source must be appropriately determined according to where and when it will be used. The size, location and type of hard surface can affect the use of the invention. Also, the lighting conditions within the area where the invention is to be used can affect the use of the invention. For example, in a well lit area such as a sun room at mid day, the present invention would require a much brighter light source than a dark hallway or gym floor. It is believed that an individual of ordinary skill could easily determine the appropriate luminescence for a particular situation or the perfect time of day or evening to use their ascertained level of luminescence. Accordingly, an embodiment of the present invention may employ a light source with varying luminescence capabilities.

Embodiments of the present invention will aid in the vacuuming, sweeping, mopping, wiping, and sweeping by hand or with dust cloth or sponge or when using a SWIFFER® (Procter and Gamble) or dustpan on any hard floor surface.

The user of the present invention will be able to effortlessly focus a beam of light at the required angle, such as parallel to the floor. The user will also be able to quickly reposition the beam of light so to be able to scan the floor and glance over the surrounding area. Embodiments of the present invention should allow the user the ability to use the apparatus on a "hands-free" basis, thereby allowing the user to utilize the product while maximizing the use of both hands.

DETAILED DESCRIPTION OF EMBODIMENTS OF THE INVENTION

The present invention will be described in detail by reference to the following examples that are provided for illustrative purposes. The following examples should not be construed as limiting the invention. Many variations that do not depart from the spirit or scope of the present invention will suggest themselves to those skilled in the art. All such obvious modifications are within the intended scope of the invention.

Example 1

A high intensity flashlight with a high output lamp that releases a brilliant, focused, smooth and level beam, preferably with high lumens of output, will be securely fastened in a removable and washable nylon sleeve fitting with an adjustable VELCRO® type hook-and-loop fastener. The bottom of the sleeve will have a soft gentle feel as to not scratch any surface. The user will first place the apparatus flat on the ground with the light facing forward and close to the surface. Then the user will step onto the bottom portion of the Velcro fastener and securely pull and tighten the VELCRO® strap, securely attaching the apparatus to the exterior side of the foot or shoe and close to the surface. Once attached, the user will turn on the light source and thereby illuminate the floor at an acute angle, using the foot to naturally aim the light beam and scan the surface to reveal small particulate matter and contaminates.

Example 2

A high intensity flashlight with a high output lamp that releases a brilliant, focused, smooth and level beam, preferably with high lumens of output, will be securely and rotatably fastened in a removable and washable nylon sleeve fitting that is attached to the end of a lightweight hand held telescopic pole. The telescopic pole allows for adjustment of varying lengths to accommodate the differing heights of potential users and well as surface locations. The rotatable attachment means such as a screw and wing nut, allows the angle of the light beam emanating from the light source to be adjusted to the optimum angle for illumination of the hard surface and the users comfort level. The end of the telescoping pole opposite the light may be equipped with a comfortable hand grip or handle. The light at the end of the telescoping pole may alternatively be equipped with a flexible head to further accommodate the optimum angle, which will account for the user's comfort. The bottom of the sleeve will have a soft gentle feel as to not damage or scratch any surface. The user will turn the device on and proceed to place the light on the hard surface or close to the hard surface being checked, at a finely tuned acute angle to reveal the unwanted small particulate and contaminates.

Example 3

A high intensity flashlight with a high output lamp that releases a brilliant, focused, smooth and level beam, preferably with high lumens of output, will be attached to the bottom surface of a commercial grade mopping bucket using a VELCRO® type attachment system. The flashlight is removably mounted on the bottom surface of the mopping bucket so that the flashlight is above the floor and angled slightly toward the floor. The wheels on the mopping bucket may acts as spacers to prevent the flashlight from directly contacting the floor. The flashlight is turned on and the light beam that emanates from the flashlight will reveal the small particulate matter and contaminates in an area directly around the mopping bucket. The user may quickly and confidentially remove the illuminated small particulate matter and contaminants in the illuminated area before mopping and moving the mopping bucket and flashlight to a new area to be illuminated and cleaned.

Example 4

A high intensity flashlight with a high output lamp that releases a brilliant, focused, smooth and level beam, preferably with high lumens of output, will be securely attached to the side of a vacuum cleaner or SWIFFER® using a custom built attachment method that will vary by make and model of vacuum cleaner or SWIFFER® that it is to be attached to. Some attachment methods may include magnetic, VELCRO® type hook and loop or factory built custom fitting that will allow the apparatus to be positioned close to the surface with the light facing forward. The bottom of the apparatus will have a soft gentle feel as to not scratch any surface. When secured to an electric vacuum cleaner, the apparatus could be built to derive power from the vacuum cleaner itself to ensure a constant energy source. The user would then turn on the light source and thereby illuminate the floor at an acute angle to reveal small particulate matter and contaminates. The user may now quickly identify and remove the illuminated small particulate matter and contaminants in the illuminated area as they vacuum or sweep with the SWIFFER®.

While certain preferred and alternative embodiments of the present invention have been set forth for purposes of disclosing the invention, modifications to the disclosed embodiments may occur to those who are skilled in the art. Accordingly, the appended claims are intended to cover all embodiments of the invention and modifications thereof which do not depart from the spirit and scope of the invention.

I claim:

1. An apparatus used to detect small particulates and contaminates on hard surfaces, comprising:
    i) a light source; and
    ii) a movable platform selected from the group consisting of a shoe, a mopping bucket, a vacuum, and a dustpan wherein the light source is attached to the movable platform so a light beam emanating from the light source contacts the hard surface at an acute angle of about 0° to about 10° and the light source is capable of emitting a focused and concentrated light beam of at least 50 lumens;
    wherein the light source is controlled by a wireless remote control.

2. The apparatus as defined in claim 1 wherein the light source is a flashlight.

3. The apparatus as defined in claim 2 wherein the flashlight is capable of emitting a focused light beam of at least 65 lumens.

4. The apparatus as defined in claim 1 wherein the movable platform is a shoe.

5. The apparatus as defined in claim 1 wherein the movable platform is a mopping bucket.

6. A method for detecting small particulate matter or contaminants on a hard surface comprising attaching a light source to a movable platform selected from a shoe, a mopping bucket, a vacuum and a dustpan, directing a beam of light from the light source at an acute angle of about 0° to about 10° onto a hard surface and illuminating the small particulate matter and contaminants on the hard surface with the beam of light wherein the light source is capable of emitting a focused and concentrated light beam of at least 50 lumens,
    wherein the light source is controlled by a wireless remote control.

7. The method as described in claim 6 wherein the movable platform is a shoe.

8. The method as defined in claim 6 further comprising the step of removing the illuminated small particulate matter and contaminants from the hard surface.

9. The method as defined in claim 8 wherein the removing step comprises further comprises mopping, sweeping, vacuuming or wiping to remove the illuminated small particulate matter and contaminants.

10. The method as defined in claim 9 wherein the removing step comprises mopping.

11. The methods as defined in claim 9 wherein the removing step comprises sweeping.

12. The apparatus of claim 1 wherein the movable platform is a vacuum.

13. The method of claim 6 wherein the movable platform is a vacuum.

14. The apparatus of claim 1 wherein the light source is capable of emitting at least 65 lumens.

15. The method of claim 6 wherein the light source is capable of emitting at least 65 lumens.

16. The apparatus of claim 1 wherein the movable platform is a dustpan.

17. The apparatus of claim 6 wherein the movable platform is a dustpan.

18. A method for cleaning small particulate matter or contaminants from a hard surface comprising:
   i) attaching a light source to a moveable platform selected from the group consisting of a shoe, a mopping bucket and a vacuum, wherein the light source is controlled by a wireless remote control,
   ii) directing a beam of light of at least 65 lumens from the light source at an acute angle of about 0° to about 10° onto the hard surface,
   iii) illuminating the small particulate matter and contaminates on the hard surface, and removing the small particulate matter or contaminants from the hard surface by mopping, sweeping, vacuuming or wiping.

* * * * *